(12) United States Patent
Bushara (10) Patent No.: US 12,161,755 B2
(45) Date of Patent: Dec. 10, 2024

(54) SUSTAINED RELEASE DEVICE FOR TREATMENT OF PARKINSON'S DISEASE AND OTHER DISORDERS

(71) Applicant: Regents of the University of Minnesota, Minneapolis, MN (US)

(72) Inventor: Khalafalla Bushara, Eden Prairie, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 21 days.

(21) Appl. No.: 17/526,609

(22) Filed: Nov. 15, 2021

(65) Prior Publication Data

US 2022/0175662 A1 Jun. 9, 2022

Related U.S. Application Data

(60) Provisional application No. 63/152,588, filed on Feb. 23, 2021, provisional application No. 63/113,856, filed on Nov. 14, 2020.

(51) Int. Cl.
*A61K 9/00* (2006.01)
*A61K 31/198* (2006.01)
*A61K 47/12* (2006.01)

(52) U.S. Cl.
CPC .............. *A61K 9/009* (2013.01); *A61K 9/006* (2013.01); *A61K 9/0065* (2013.01); *A61K 31/198* (2013.01); *A61K 47/12* (2013.01)

(58) Field of Classification Search
CPC ...... A61K 31/198; A61K 47/12; A61K 9/006; A61K 9/0065; A61K 9/009
See application file for complete search history.

(56) References Cited

U.S. PATENT DOCUMENTS

| | | | |
|---|---|---|---|
| 5,194,003 A | 3/1993 | Garay et al. | |
| 10,688,058 B2 | 6/2020 | Hsu et al. | |
| 10,813,880 B2 | 10/2020 | Tan et al. | |
| 10,814,108 B2 | 10/2020 | Kaufman et al. | |
| 10,829,621 B2 | 11/2020 | Lee et al. | |
| 2004/0029777 A1* | 2/2004 | Ando | A61K 31/404 514/570 |
| 2007/0062549 A1* | 3/2007 | Holton | A24B 15/28 131/352 |
| 2008/0299197 A1* | 12/2008 | Toneguzzo | A61K 9/0004 514/567 |
| 2010/0247586 A1* | 9/2010 | Hugerth | A61K 31/465 424/440 |
| 2018/0057229 A1* | 3/2018 | St. Lawrence | B65B 51/26 |
| 2019/0224143 A1* | 7/2019 | Velip | A61K 31/00 |
| 2020/0289402 A1 | 9/2020 | Schmitz et al. | |
| 2020/0297026 A1 | 9/2020 | Kannisto et al. | |
| 2021/0267739 A1 | 9/2021 | Heller et al. | |

FOREIGN PATENT DOCUMENTS

| | | | |
|---|---|---|---|
| EP | 1663168 A2 | 6/2006 | |
| ES | 2754047 A1 | 4/2020 | |

OTHER PUBLICATIONS

Nagayama, Hiroshi et al, The Effect of Ascorbic Acid on the Pharmacokinetics of Levodopa in Elderly Patients with Parkinson Disease, Clinical Neuropharmacology 27(6), 2004, pp. 270-273 (Year: 2004).*
Barua, S., et al., "Drug delivery techniques for buccal route: formulation strategies and recent advances in dosage form design", Journal of Pharmaceutical Investigation 46, 593-613 (2016).
Biopharma Dive, "Sunovion crowds a new group of Parkinson's drugs, with uncertain sales prospects", https://www.biopharmadive.com/news/parkinsons-drugs-sunovion-fda-approval/578514, 4 pages (2020).
Biospace, "Parkinson's disease Therapeutics Market: Levodopa combination drugs to be an attractive product segment", https://www.biospace.com/article/parkinson-s-disease-therapeutics-market-levodopa-combination-drugs-to-be-an-attractive-product-segment/, 10 pages (2020).
Carter, J, et al., "Cost-effectiveness of subdermal implantable buprenorphine versus sublingual buprenorphine to reat opioid use disorder", Journal of Medical Economics 20(8), 893-901 (2017).
Cutler, R, et al., "Economic impact of medication non-adherence by disease groups: a systematic review", BMJ Open 8(1), e016982, (2018).
Duopa, Label and Full Prescribing Information, Reference ID: 4611736, Smiths Medical, 112 pages (2015).
Eggert, K, et al., "Continuous jejunal levodopa infusion in patients with advanced parkinson disease: practical aspects and outcome of motor and non-motor complications", Clin Neuropharmacol 31(3), 151-166 (2008).
FDA, "Drug Approval Package: KYNMOBI", Drug Approvals and Databases, https://www.accessdata.fda.gov/drugsatfda_docs/nda/2020/210875Orig1s000TOC.cfm, 2 pages (2020).
FDA, "Duopa (carbidopa and levodopa) Enteral Suspension", Drug Approvals and Databases, https://www.accessdata.fda.gov/drugsatfda_docs/nda/2015/203952Orig1s000TOC.cfm, 1 page (2015).
FDA, "Mifeprex (Mifepristone) Tablets", Drug Approvals and Databases, https://www.accessdata.fda.gov/drugsatfda_docs/nda/2016/020687Orig1s020TOC.cfm, 1 page (2016).

(Continued)

*Primary Examiner* — Brian-Yong S Kwon
*Assistant Examiner* — Lyndsey M Beckhardt
(74) *Attorney, Agent, or Firm* — Viksnins Harris Padys Malen LLP (57) ABSTRACT

Provided herewith is a device having one sachet or more than one nested sachet with the largest sachet made of, e.g., a non-dissolvable, porous, wettable and non-toxic material. The sachets are filled with a desired combination of medications and excipients to provide sustained dosing, blood levels and effects of the said combination of medications. The sachets can be arranged in such a configuration to be suitable for placement in the oral/buccal cavity with comfort and to deliver, e.g., continuous or on-demand release of the desired medications for both transmucosal and gastrointestinal absorption. Also provided are containers for such devices.

16 Claims, 3 Drawing Sheets

(56) References Cited

OTHER PUBLICATIONS

FDA, "Nonclinical Safety Evaluation of Reformulated Drug Products and Products Intended for Administration by an Alternate Route", U.S. Department of Health and Human Services, Food and Drug Administration Center for Drug Evaluation and Research (CDER), Pharmacology/Toxicology, 12 pages (Oct. 2015).

Hearnden, V, et al., "New developments and opportunities in oral mucosal drug delivery for local and systemic disease", Adv Drug Deliv Rev 64(1), 16-28 (2012).

Itin, C, et al., "Controlled Delivery of Apomorphine Through Buccal Mucosa, Towards a Noninvasive Administration Method in Parkinson's Disease: A Preclinical Mechanistic Study", Journal of Pharmaceutical Sciences 109, 2729-2734 (2020).

Jankovic, J, et al., "Transdermal rotigotine: double-blind, placebo-controlled trial in Parkinson disease", Arch Neurol 64 (5), 676-682 (2007).

Kaul, M, et al., "An Overview on Buccal Drug Delivery System", IJPSR 2(6), 1303-1321 (2011).

Luinstra, M, et al., "Pharmacokinetics and tolerability of inhaled levodopa from a new dry-powder inhaler in patients with Parkinson's disease", Ther Adv Chronic Dis 10, 1-10 (2019).

Meglio, M, "Subcutaneous Levodopa/Carbidopa Delivery Provides Potential Breakthrough in Parkinson Disease", NeurologyLive, https://www.neurologylive.com/view/subcutaneous-levodopa-carbidopa-delivery-provides-potential-breakthrough-in-parkinson-disease, 3 pages (2021).

Nyholm, D, et al., "Duodenal levodopa infusion monotherapy vs oral polypharmacy in advanced Parkinson disease", Neurology 64(2), 216-223 (2005).

Pather, S, et al., "Current status and the future of buccal drug delivery systems", Expert Opin. Drug Deliv. 5(5), 1-12 (2008).

Pilicheva, B, et al., "Layer-by-layer self-assembly films for buccal drug delivery: The effect of polymer cross-linking", Journal of Drug Delivery Science and Technology 59 (101897) (2020).

Poewe, W, et al., "Novel formulations and modes of delivery of levodopa", Movement Disorders 30(1), 114-120 (2015).

Pons-Faudoa, F, et al., "Advanced implantable drug delivery technologies: transforming the clinical landscape of therapeutics for chronic diseases", Biomed Microdevices 21(2), 47, 46 pages (2020).

Slomski, A., et al., "Sublingual Apomorphine Manages Parkinson Disease Off Episodes", JAMA 323 (8), 701 (2020).

Tompson, D, et al., "Steady-state pharmacokinetic properties of a 24-hour prolonged-release formulation of ropinirole: results of two randomized studies in patients with Parkinson's disease", Clin Ther 29(12), 2654-2666 (2007).

Verhagen, L, et al., "Gastroretentive carbidopa/levodopa, DM-1992, for the treatment of advanced Parkinson's disease", Mov Disord 30 (9), 1222-1228 (2015).

* cited by examiner

SUSTAINED RELEASE DEVICE FOR TREATMENT OF PARKINSON'S DISEASE AND OTHER DISORDERS

CROSS-REFERENCE TO RELATED APPLICATIONS

This application claims priority to U.S. Provisional Application No. 63/113,856 that was filed on Nov. 14, 2020; and U.S. Provisional Application No. 63/152,588 that was filed on Feb. 23, 2021. The entire content of the applications referenced above are hereby incorporated by reference herein.

BACKGROUND

The symptoms of many disorders can be effectively ameliorated by taking medications. However, the blood levels of such medications can fluctuate between peaks and troughs if given orally, leading to variable control of symptoms. An important example of this problem is in the treatment neurological disorders, such as Parkinson's disease, in which the benefit from orally administered medications is often short lived, leading to frequent dosing, which can be inconvenient and negatively affects compliance and quality of life. Sustained release formulations taken orally (such as Sinemet products) including gastric retentive methods only have limited success (Verhagen et al., Mov Disord., 30(9), 1222-8 (2015)). Skin absorption via medicated patches has been used, however only few medications can reliably be absorbed through the skin such as rotigotine (Jankovic et al., Arch Neurol., 64(5), 676-82 (2007)). These are dopamine agonists and often result in skin irritation and other side-effects. Sublingual medications such apomorphine and inhaled medications such as levodopa have recently been introduced. However, the aim of these formulations has been the rapid release and absorption of the medication as a "rescue" for off periods (Luinstra et al., Ther Adv Chronic Dis. 2019; 10:2040622319857617; Slomski et al., JAMA, 323(8), 701 (2020)). A system delivering levodopa via a gastric tube has also been introduced (Eggert et al., Clin Neuropharmacol., 31(3), 151-66 (2008); Nyholm et al., Neurology, 64(2), 216-23 (2005)). However, this requires an invasive procedure with multiple risks and side effects.

Therefore, there remains a critical need for convenient methods and devices for delivering sustained amounts medications with an acceptable side effect profile to control the symptoms.

SUMMARY OF CERTAIN EMBODIMENTS

Accordingly, to meet these needs, provided herein are devices that comprise at least a first sachet nested inside a second sachet, wherein each sachet can be independently made of porous, wettable and non-toxic materials, wherein each sachet comprises an effective amount (e.g., therapeutically effective amount) of a medication selected to treat a disease or condition, wherein the device is configured in a shape and size such that the device can be placed in the mouth of a human subject. Certain embodiments provide a storing and dispensing container as described herein for use with such devices.

BRIEF DESCRIPTION OF THE FIGURES

FIGS. 1A-1C. FIGS. 1A-1C illustrate views of devices, in accordance with at least one example of the present subject matter. Not drawn to scale or exact shape. Actual assembly size: 5-50 mm in length, 5-20 mm in width and 2-10 mm in height. 1A Sachets. 1B and 1C Cross-sectional view of nested sachets.

FIG. 2A-2B. FIGS. 2A-2B illustrate views of a device, in accordance with at least one example of the present subject matter. Not drawn to scale or exact shape. Actual assembly size: 5-50 mm in length, 5-20 mm in width and 2-10 mm in height. 2A Sachets. 2B Separable sachets.

FIG. 3: 1—Smaller (inner) sachet content hopper/container. 2. Connection (measured amount dispenser—not shown). 3. Permeable material in the form of flat tape (guiding frame for folding flat tape into tube—not shown). 4. Permeable material in the form of continuous tube wrapped around content dispenser (vertical sealer—not shown). 5 Sealing apparatus. 6. Cutting apparatus. 7. Individual filled and sealed smaller (inner) sachets. 8. Container of filled smaller sachets. 9. Permeable material in the form of flat tape (guiding frame for folding flat tape into tube—not shown). 10. Permeable material in the form of continuous tube wrapped around content dispenser (vertical sealer—not shown). 11. Filled and sealed smaller (inner) sachets inserted within the tube of permeable material. 12. Opening and connection for passage of filled and sealed smaller sachets. 13. Opening for passage of content of larger (outer) sachet (12 and 13 show double lumen in dotted circles). 14. Larger sachet content hopper/container 15. Connection for filling larger sachets (measured amount dispenser—not shown). 16. Individual multiple-sachet assembly filled with a smaller (inner) sachet (from container 8) and contents (from container 14).

FIG. 4: 1: Sachets in a string of sachets arranged in a spiral (guided by a spiral frame—not shown). 2: The sachet closest to the opening, 3: a continuation/extension of the frame to direct the sachet through the opening. 4: a gear/disk with rough surface in contact with sachets. 5: A prominence on the surface of the container. 6. A lever (part of or connected with the prominence (5) in contact with the gear/disk when the prominence is pushed down in a diagonal direction (black arrows). 7: a sachet pushed outside the container through the aperture. 8: The container.

DETAILED DESCRIPTION

Certain embodiments of the present invention provide devices that comprise at least a first sachet nested inside a second sachet, wherein each sachet is made of porous, wettable and non-toxic materials, wherein each sachet comprises an effective amount of a medication selected to treat a disease or condition, wherein the device is configured in a shape and size such that the device can be placed in the mouth of a human subject.

In certain embodiments, the device is configured in a shape and size such that the device can be placed in the buccal cavity of the subject.

In certain embodiments, the second sachet is configured in a shape and size of 5-50 mm in length, 5-20 mm in width and/or 2-10 mm in width.

In certain embodiments, the second sachet is configured to maximize comfort and minimize deformity of the lips and cheeks for discreet use.

In certain embodiments, the second sachet is made of non-dissolvable, porous and permeable material.

In certain embodiments, the first sachet is made of dissolvable, partially dissolvable or non-dissolvable, porous and permeable material.

In certain embodiments, the second sachet is made of dissolvable, partially dissolvable or non-dissolvable, porous and permeable material.

In certain embodiments, the first and second sachets vary in content of medication to achieve the desired pharmaceutical effect (such as pre-medication and priming).

In certain embodiments, the first and second sachets differ in permeability, porosity, dissolvability and structure of the material.

In certain embodiments, the second sachet is made of a material with smooth outer surface for maximum comfort.

In certain embodiments, at least one or both the first and second sachet is made of a non-toxic material.

In certain embodiments, at least one or both the first and second sachet is made of a biodegradable, natural material.

In certain embodiments, at least one or both the first and second sachet is made of cellulose fiber filter paper.

In certain embodiments, at least one or both the first and second sachet is made of corn fiber filter paper.

In certain embodiments, at least one or both the first and second sachet is made of carboxymethyl cellulose.

In certain embodiments, at least one or both the first and second sachet is made of plant fiber filter paper.

In certain embodiments, the material of at least one or both the first and second sachet is unbleached and processed by non-chemical sterilization and drying processes such as UV and infrared methods.

In certain embodiments, at least one or both the first and second sachet is made of non-toxic synthetic polymers.

In certain embodiments, at least one or both the first and second sachet can optionally be configured such that the patient has some control on the release of active ingredient by applying positive or negative pressure (e.g., sucking) with the tongue or cheek/lip muscles to increase the release.

In certain embodiments, at least one or both the first and second sachet can optionally be configured such that the patient has some control on the release of active ingredient by increasing the wetness of the device to increase the release of contents.

In certain embodiments, at least one or both the first and second sachet can optionally be configured in a shape and size such that the patient can move the device (e.g., with the tongue and mouth muscles) to the sublingual area to increase the absorption of the active medications.

In certain embodiments, at least one or both the first and second sachet can optionally be configured in a shape and size such that the patient can remove the device from the mouth with ease (e.g., manually or by spitting) to end the absorption of the active medications or in order to replace the device with another.

In certain embodiments, at least one or both the first and second sachet can optionally be configured in a shape, size and color such that the patient can remove the device from the mouth in a discreet manner.

In certain embodiments, at least one or both the first and second sachet can optionally be configured in a shape and size such that the patient can apply/use more than one device at a time.

In certain embodiments, the second (outer) sachet comprises an outer surface having an adhesive property. In certain embodiments, the second sachet is made of a material with an outer surface having an adhesive property. Examples of materials that can provide an adhesive property include adhesive polymers such as thiolated poly(acrylic acid), poloxamer, celluloseacetophthalate, methyl cellulose, hydroxy ethyl cellulose, poly(amidoamine) dendrimers, poly(dimethyl siloxane) and polyvinyl pyrrolidone). The adhesive property can reduce the risk of dislodging the sachet in the mouth.

In certain embodiments, the second (outer) sachet does not comprise an outer surface having an adhesive property. In certain embodiments, the second sachet is made of a material without an outer surface having an adhesive property.

In certain embodiments, at least one or both the first and second sachet can optionally be configured in a shape and size such that the device is easily divisible into two or more smaller devices to reduce the dose of the desired medications.

In certain embodiments, at least one or both the first and second sachet is partially filled with a non-toxic material such as plant fiber to help maintain the bulk and shape of the device.

In certain embodiments, at least one or both the first and second sachet is partially filled with stabilizers and fillers to maintain consistency such as plant fiber, dried herbs such as mint leaves, ginger roots, citrus fruit peel or pulp, dried leaves, dried flowers, dried stems, dried seeds, dried roots, dried peel, dried fruits and vegetables.

In certain embodiments, at least one or both the first and second sachet is filled with a humectant material such as propylene glycol, hexylene glycol, butylene glycol, aloe vera gel, Alpha hydroxy acids such as lactic acid, glyceryl triacetate, honey, lithium chloride, molasses, polymeric polyols such as polydextrose, quillaia, sodium hexametaphosphate E452i, urea, castor oil and sugar alcohols (sugar polyols) such as glycerol, sorbitol, xylitol, maltitol, mannitol or erythritol.

In certain embodiments, at least one or both the first and second sachet is filled with a material moistened with water or other liquid to help with varying the rate of release of medications.

In certain embodiments, at least one or both the first and second sachet is filled with a material such as salt, sweeteners, mint or other herbs, dried leaves, dried flowers, dried stems, dried seeds, dried roots, dried fruits, dried vegetables, spices or flavoring agents to improve taste and palatability.

In certain embodiments, at least one or both the first and second sachet is filled with excipients to improve solubility, disintegration, friability, mucosal soothing, mucosal absorption and gastrointestinal absorption.

In certain embodiments, at least one or both the first and second sachet is filled with excipients to adjust the acidity/alkalinity (PH).

In certain embodiments, at least one or both the first and second sachet contains inactive ingredients including one or any combination of excipients such as cellulose, hydroxypropyl cellulose, hydroxyethyl cellulose, microcrystalline cellulose, hypromellose, carmellose sodium, magnesium stearate, crospovidone, glycerol, glyceryl monostearate, starch, pregelatinized starch, maltodextrin, mannitol, erythritol, sodium hydroxide, sodium metabisulfite, disodium EDTA, sucralose, aspartame, polyvinylacetate-crotonic acid copolymer, 1,2-dipalmitoyl-sn-glycero-3-phosphocholine (DPPC), colloidal silicon dioxide, docusate sodium, sodium benzoate, sodium starch glycolate, ascorbic acid, stearic acid, hydrochloric acid, citric acid anhydrous, glycerin, methylparaben, propylparaben, sodium citrate dihydrate, sodium citrate, sodium hydroxide, sodium bicarbonate.

In certain embodiments, at least one or both the first and second sachet contains one or any combination of acid derived from orange juice, lemon, lime, pineapple, rhubarb and other acidic fruits, vegetables and plants including carboxylic acid, tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic acid, boric acid and mixtures thereof.

In certain embodiments, at least one or both the first and second sachet contains inactive ingredients including carriers, surfactants (surface active agents), thickening agents, emulsifying agents, binding agents, dispersion or suspension agents, buffering agents, penetration-enhancing agents, solubilizers, colorants, sweeteners, flavoring agents, coatings, disintegrating agents, lubricants, preservatives, isotonic agents, and combinations thereof.

In certain embodiments, at least one or both the first and second sachet is filled with dissolvable particles, spheres, pellets, granules containing medicines to control the release of medicines.

In certain embodiments, each sachet comprises levodopa.

In certain embodiments, the sachets are filled with a combination of levodopa and carbidopa.

In certain embodiments, the sachets are filled with a combination of levodopa, carbidopa and ginger.

In certain embodiments, the sachets are filled with a combination of levodopa, carbidopa, ginger and an anticholinergic medication such as atropine, scopolamine diphenhydramine, meclizine, buclizine, cyclizine, hydroxyzine, pirenzepine, benztropine, atropine, hyoscyamine, butylscopolamine, methylscopolamine, doxylamine, promethazine, trihexyphenidyl or orphenadrine to both treat Parkinson's disease and reduce nausea and act locally to reduce salivation.

In certain embodiments, the sachets are filled with a combination of levodopa, carbidopa and ascorbic acid for its effect in reducing levodopa-induced neurotoxicity.

In certain embodiments, the sachets are filled with primidone for treatment of tremor.

In certain embodiments, the sachets are filled with an anti-tremor medication including primidone and a beta blocker such as propranolol, Acebutolol, atenolol, betaxolol, bisoprolol, carteolol, carvedilol, labetalol, metoprolol, nadolol, nebivolol, penbutolol, pindolol, sotalol or timolol.

In certain embodiments, the sachets are filled with anti-tremor medications including topiramate, zonisomide, primidone and a beta blocker such as propranolol, Acebutolol, atenolol, betaxolol, bisoprolol, carteolol, carvedilol, labetalol, metoprolol, nadolol, nebivolol, penbutolol, pindolol, sotalol or timolol.

In certain embodiments, the sachets are filled with a beta blocker such as propranolol, Acebutolol, atenolol, betaxolol, bisoprolol, carteolol, carvedilol, labetalol, metoprolol, nadolol, nebivolol, penbutolol, pindolol, sotalol or timolol.

In certain embodiments, the sachets are filled with baclofen for treatment of spasticity and muscle cramps.

In certain embodiments, the sachets are filled with a medication to treat vertigo.

In certain embodiments, the sachets are filled with a medication to treat episodic ataxia.

In certain embodiments, the sachets are filled with a medication to treat vertebrobasilar migraine.

In certain embodiments, the sachets are filled with analgesics such as non-steroidal anti-inflammatory medications.

In certain embodiments, the sachets are filled with analgesics such as morphine or its derivatives.

In certain embodiments, the sachets are filled with anti-migraine medications such as triptans, anti-nausea medications and analgesics.

In certain embodiments, the sachets are filled with cannabis or its natural or synthetic derivatives for treatment of tics, tremor, muscle spasms and other conditions.

In certain embodiments, the sachets are filled with anti-anxiety medications such as benzodiazepines and betablockers.

In certain embodiments, the sachets are filled with anti-performance anxiety medications such as betablockers.

In certain embodiments, the sachets are filled with an erectile dysfunction medication.

In certain embodiments, the sachets are filled with a premature ejaculation medication.

In certain embodiments, the sachets are filled with stimulant medications to treat conditions such as fatigue, sleepiness, narcolepsy and attention deficits disorders.

In certain embodiments, the sachets are filled with medications for overactive bladder and urinary incontinence.

In certain embodiments, the sachets are filled with medications used to premedicate for infusions such as reclast and iron infusion.

In certain embodiments, the sachets are filled with medications used to premedicate for chemotherapy.

In certain embodiments, the sachets are filled with medications used to premedicate for allergy immunotherapy.

In certain embodiments, the sachets are filled with medications used to treat premenstrual syndrome.

In certain embodiments, the sachets are filled with medications used to treat symptoms of postmenopausal syndrome such as hot flashes.

In certain embodiments, the sachets are filled with medications used to treat diarrhea and irritable bowel syndrome.

In certain embodiments, the sachets are filled with medications used to treat itching, pruritis and urticaria.

In certain embodiments, the sachets are filled with medications used to treat nausea from pregnancy.

In certain embodiments, the sachets are filled with medications used to prevent and treat nausea from infusions.

In certain embodiments, the sachets are filled with medications used to treat cardiac arrhythmias.

In certain embodiments, the sachets are filled with medications used to treat dry mouth and xerostomia.

In certain embodiments, the sachets are filled with medications used to treat claustrophobia for magnetic resonance scanning.

In certain embodiments, the sachets are filled with medications used to treat addictive disorders such as smoking, gambling and binge eating disorder.

In certain embodiments, the sachets are filled with medications used to prevent craving in addictive disorders.

In certain embodiments, the sachets are filled with medications used to treat myasthenia gravis.

In certain embodiments, the sachets are filled with medications used to treat asthma.

In certain embodiments, the sachets are filled with medications used to treat gastroesophageal reflux, heartburn and indigestion.

In certain embodiments, the sachets are filled with a therapeutically effective combination of any of the active and inactive ingredients described herein.

In certain embodiments, the storing and dispensing container comprises a string of devices of sachets described herein.

As used herein, a sachet is a small bag or packet. The sachet can be sealed with the desired contents inside.

As used herein, nested refers to being fitted inside. For example, a larger outer sachet may contain any number smaller sachets fitted in each other or beside each other within the outer sachet.

The dimensions of the sachet can be, e.g., 1-50 mm in length, 1-20 mm in width and 1-10 mm in height.

The general shape of each sachet can, in certain embodiments be, pillow shape, rectangular, oval, rounded rectangle, crescent shape or irregular shape.

The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The term "carrier" refers to a diluent, excipient, or vehicle with which an active compound is administered. Such pharmaceutical carriers can be liquids, such as water, saline solutions, aqueous dextrose solutions, aqueous glycerol solutions, and lipids and oils, including those of petroleum, animal, vegetable or synthetic origin. Suitable pharmaceutical carriers are described in "Remington's Pharmaceutical Sciences" by E. W. Martin, 18th Edition. The disclosure is incorporated herein by reference.

Certain embodiments provide a device comprising one sachet or more than one nested sachets made of porous, wettable and non-toxic material, to be filled with the desired combination of medications. The device can be arranged in such a configuration so that it is placed intraorally with comfort to function as a convenient delivery method that provides sustained dosing of the desired combination of medications and delivers continuous and on-demand release of the said combination of medications for both oral/buccal transmucosal absorption and gastrointestinal absorption.

In certain embodiments, the device comprises one sachet or more than one nested sachet made of porous, non-dissolvable, wettable and non-toxic material to be filled with the desired combination of medications and other ingredients and materials to improve the taste, palatability, solubility and mucosal absorption of the desired medication.

In certain embodiments, the device is configured with a shape and size to be placed comfortably and discreetly in the buccal cavity between the cheek and gum or under the upper or lower lip.

In certain embodiments, if the device gets wet, the desired medication is dissolved by the saliva and released slowly and continuously onto the buccal mucosa where it is absorbed locally and swallowed to be absorbed in the gastrointestinal tract.

In certain embodiments, the device can be used to deliver a medication or a combination of medications to treat Parkinson's disease and associated excessive salivation and medication-induced nausea.

In certain embodiments, the device can be used to deliver a medication or a combination of medications to treat tremor, tics, muscle spasticity and other conditions and symptoms such as pain, nausea and anxiety.

In certain embodiments, the user will have some control on the release of the medication(s) to achieve the desired effect by applying positive or negative pressure with the cheek, lips or tongue or by moving the device to other parts of the oral cavity such as the sublingual area.

In certain embodiments, the user will have some control on the duration of release of the medication(s) to achieve the desired effect by removing the device.

In certain embodiments, the medication(s) is(are) micronized, nano-milled or spray-dried.

In certain embodiments, the particle size of the medication(s) is(are) (d50-d90) 1-30 microns.

In certain embodiments, the current invention provides unique and useful advances by using a new formulation and delivery method of carbidopa/levodopa, the gold standard of Parkinson's disease treatment. The current invention is also unique in that it utilizes both transmucosal and gastrointestinal absorption to provide a sustained release system. Levodopa, similar to L-amino acids are known to be absorbed transmucosaly (Vadgama et al., Amino Acids, 3(3), 271-86 (1992)).

Transmucosal absorption allows direct access of drugs to the systemic circulation, thus bypassing gastrointestinal degradation and liver metabolism. The sublingual region allows rapid drug absorption for immediate release formulations, while the buccal route between the cheek and teeth and gums can be utilized for more sustained drug release. These buccoadhesive dosage forms utilize mucoadhesive crosslinked hydrogels (such as carbopol, polycarbophil) that interact with buccal mucus and adhere to the mucous lining (mucoadhesive or buccoadhesive systems). The aim of these complex formulations is to control the release of the active drug and to minimize its escape into the oral cavity and its ingestion. The current invention avoids this particular limitation by using formulations and delivery methods that are compatible with both the buccomucosal absorption and gastrointestinal absorption of the active drug.

A major drawback of sublingual and buccal methods is that the amount of active medication used is limited. The delivery method disclosed herein allows for both rapid and slow release. The patient has some control on the release of active ingredient by applying positive or negative pressure with the tongue or cheek/lip muscles to increase the release, or by moving the device to the sublingual area to increase the absorption. In this regard, the delivery method of the current invention has the advantages of liquid carbidopai-levodopa suspension, which allows for on-demand rapid dosing of levodopa liquid suspension, which is absorbed faster than swallowed tablets that require time for disintegration and their absorption is delayed by slow gastric emptying (Ngwuluka et al., Expert Opin Drug Deliv.; 7(2), 203-24 (2010)). Taking sips of liquid levodopa has anecdotally proven effective, however, it is an inconvenient method requiring carrying a liquid container which may also need to be refrigerated (Kurth et al., Neurology 43(5), 1036-9 (1993); Lopez et al., Neurologia, 10(4), 155-8 (1995)). Other anecdotal methods to achieve faster absorption of levodopa and minimize gait freezing include chewing the tablets, dissolving the tablets under the tongue or even snorting the crushed tablets (Ngwuluka et al., Expert Opin Drug Deliv.; 7(2), 203-24 (2010); Bhirud et al., Indian J Anaesth, 61(5), 432-4 (2017)). Administration of carbidopa levodopa rectally was much less effective, with significantly poor absorption of carbidopa. However, in retrospect and in view of the new technology presented herein, it confirms the absorbability of levodopa transmucosaly (Vogelzang et al., Case Rep Neurol, 7(3), 209-12 (2015); Beasley et al., N Engl J Med, 289(17), 919 (1973)). Therefore, the new technology described herein is superior to liquid, oral dissolving or disintegrating tablets methods as it allows for both transmucosal/buccal rapid absorption (continuously and on-demand) and faster gastrointestinal absorption (continuously and on-demand).

The delivery method disclosed herein also allows for convenient removal and replacement of the device without requiring, e.g., drinking a liquid to swallow pills or removing the clothes to replace a skin patch. Removal of the device with ease also enables the patient to end the dosing of the medications on demand (e.g., when dyskinesia develops from overmedicating with levodopa). This is beneficial to end the effect of medications in other conditions, for example when using a beta blocker for performance anxiety, e.g., stage fright.

The delivery method disclosed herein will be particularly beneficial for the treatment of disorders that require as needed temporary control of symptoms such as anxiety attacks, panic attacks, performance anxiety, claustrophobia (e.g., for MRI scanning), erectile dysfunction, premature ejaculation, vertigo, headaches, pain and temporary pain-control for procedures.

The delivery method disclosed herein further allows for the release of different medications in a sequential and convenient manner to achieve the desired effect. This allows for the control of each medication's release and therefore onset and duration of action. For example, pre-treatment of Parkinson's disease patients with carbidopa significantly increases the level of levodopa and prolongs its half-life. Sequential administration of medications is also known to be beneficial when a combination, or cocktail, of medications is given to premedicate patients for procedures such as allergy immunotherapy, contrast dye, blood-transfusion, chemotherapy and other infusion therapy.

Certain embodiments of the invention will now be illustrated by the following non-limiting Examples.

EXAMPLES

Convenient delivery methods that provide sustained dosing of the desired combination of medications and include a device that delivers continuous release of said combination of medications for both buccal mucosal and gastrointestinal absorption.

Example 1

In Example 1, a device comprises a sachet or nested sachets made of porous material, each filled with the desired combination of medications. The device is placed in the buccal cavity for example between the cheek and gum or under the upper or lower lip to provide continuous, and if desired, sequential release of medications.

Example 2

In Example 2, the device of Example 1 can optionally be configured in a shape and size that minimizes deformity of the lips or cheeks for discreet use.

Example 3

In Example 3, the device of Example 1 can optionally made of a non-dissolvable, wettable, biodegradable, non-toxic natural material such as cellulose or corn fiber filter paper, unbleached and processed by UV sterilization and infrared drying.

Example 4

In Example 4, the device of any one or any combination of Examples 1-3 can be filled with a combination of levodopa and carbidopa to treat Parkinson's disease, restless legs syndrome and dopa-responsive dystonia.

Example 5

In Example 5, the device of any one or any combination of Examples 1-3 can be filled with a combination of levodopa, carbidopa and ginger for its anti-emetic properties to treat Parkinson's disease.

Example 6

In Example 6, the device of any one or any combination of Examples 1-3 can be filled with a combination of levodopa, carbidopa, ginger and an anticholinergic medication such as atropine, scopolamine or hyoscine to both treat Parkinson's disease and reduce nausea and salivation.

Example 7

In Example 7, the device of any one or any combination of Examples 1-3 can be filled with baclofen to treat spasticity.

Example 8

In Example 8, the device of any one or any combination of Examples 1-3 can be filled with primidone and/or a beta blocker to treat essential tremor, other types of tremor or stage fright.

Example 9

In Example 9, the device of any one or any combination of Examples 1-3 can be filled with analgesics such as morphine or its natural or synthetic derivatives.

Example 10

In Example 10, the device of any one or any combination of Examples 1-3 can be filled with analgesics such as non-steroidal anti-inflammatory medications.

Example 11

In Example 11, the device of any one or any combination of Examples 1-3 can be filled with cannabis or its natural or synthetic derivatives to treat tics, pain and/or tremor.

Example 12

In Example 12, the device of any one or any combination of Examples 1-3 can be filled with a material such as plant fiber to help with maintain the shape of the device.

Example 13

In Example 13, the device of any one or any combination of Examples 1-3 can be filled with a moist material such as plant fiber+water or other liquid to help with the slow release of medications.

Example 14

In Example 14, the device of any one or any combination of Examples 1-3 can be filled with a material such as salt, sweeteners, mint or other herbs, taste enhancers, spices or flavoring agents to improve taste and palatability.

Example 15

In Example 15, the device of any one or any combination of Examples 1-3 can be filled with an excipient to improve solubility and mucosal soothing and absorption.

Example 16

In Example 16, the device of any one or any combination of Examples 1-3 can be filled with an excipient material to delay the release of desired medications.

Example 17

Example 17 describes one embodiment of the invention that can be used to treat Parkinson's Disease. This example provides a device that includes an assembly of two nested sachets with the combination of carbidopa (CD) and levodopa (LD) in the inner sachet that varies from that in the outer sachet. This allows for sequential release of CD and then LD to mimic a CD pretreatment method, which increases LD absorption and prolongs its half-life. The outer sachet can contain about 0 to 200 mg of CD and about 0 to 400 mg of LD, and the inner sachet can contain about 0 to 200 mg of CD and about 400 to 1200 mg of LD. The assembly may also contain vitamin C, which can increase the acidity and thus solubility of LD and CD and can be used as an antioxidant. The assembly may further contain mannitol (used as a sweetener and to increase moisture and reduces saliva barrier to enhance buccal absorption), sodium citrate (used to increase LD solubility and as a source of sodium which is important for both L-amino acid and ascorbic acid transmucosal buccal absorption), dried ginger root fibers (used for an anti-emetic effect and to increase local saliva production) and mint dried leaves (to improving flavor and palatability and as a source of L-menthol, a permeation enhancer to increase buccal absorption). Similar to erythritol, mannitol is resistant to bacterial breakdown and, therefore, minimizes the risk of tooth decay. Mannitol may also function to improve PD symptoms, including anosmia. The total size of assembly can be 12-20 mm×2-4 mm×30-50 mm, with the inner sachet having a size of 5-12 mm×1-3 mm×20-42 mm. Contents are distributed as 1.8-2.6 ml for the outer sachet and 0.5 to 1.5 ml for inner sachet.

Example 18

Figure 3:
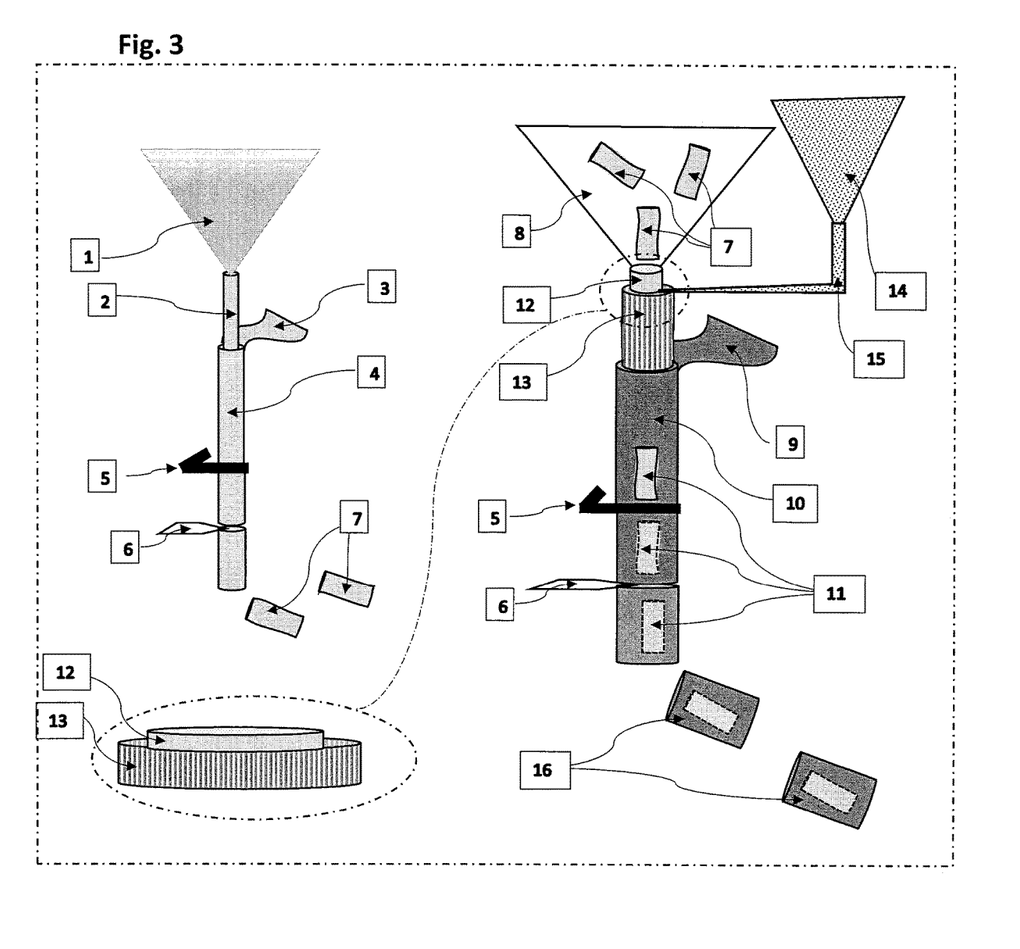

Example 18 and FIG. 3 describe examples of the manufacturing of nested sachets. The manufacturing and filling of sachets can utilize high speed vertical or horizontal filling machines. This can involve filling, sealing and cutting processes and automated methods for manufacturing small sachets made of a permeable material and filled with a mixture of ingredients (see, e.g., Paules et al., U.S. Pat. No. 8,757,167 and Petkov et al., EP 1 161 367). The process can involve providing the permeable material in a tape form configured into a continuous tube wrapped around a filling tube that injects the filling ingredients into the permeable material tube. A heat-sealing mechanism can then divide the filled permeable material tube into a string of sachets. A cutting mechanism produces individual filled sachets. Disclosed herein is a significant modification of these processes to produce assemblies of multiple nested sachets.

The smaller (inner) sachets are produced by a filling mechanism. The filled smaller sachets are then fed into another double lumen filling tube with an inner lumen for passage of smaller sachets and a surrounding outer lumen for passage of ingredients to fill the larger (outer) sachet. The permeable material tube (surrounding the outer lumen) is then divided into individual assemblies by a sealing and a cutting mechanism. The apparatus can be further equipped with containers, tubes, sensors, motors, pneumatic functions, stirring, vibrating and conveying mechanisms to accomplish inserting precise quantities of the filling ingredients into the sachets and inserting smaller sachets into the larger outer sachets.

The process described herein is different from the current processes in that the filling tube will be compromised of double lumen with an inner lumen for insertion of smaller inner sachets into the larger sachet while the lager lumen functions as a filling tube to insert precise quantities of ingredients into the larger sachet surrounding the smaller inner sachet. Thus, the process involves two containers (hoppers): one contains filled small sachets while the other contains ingredients for filling the larger outer sachet (FIG. 3). Accordingly, certain embodiments of the invention are directed to the process described herein.

Example 19

Figure 4:
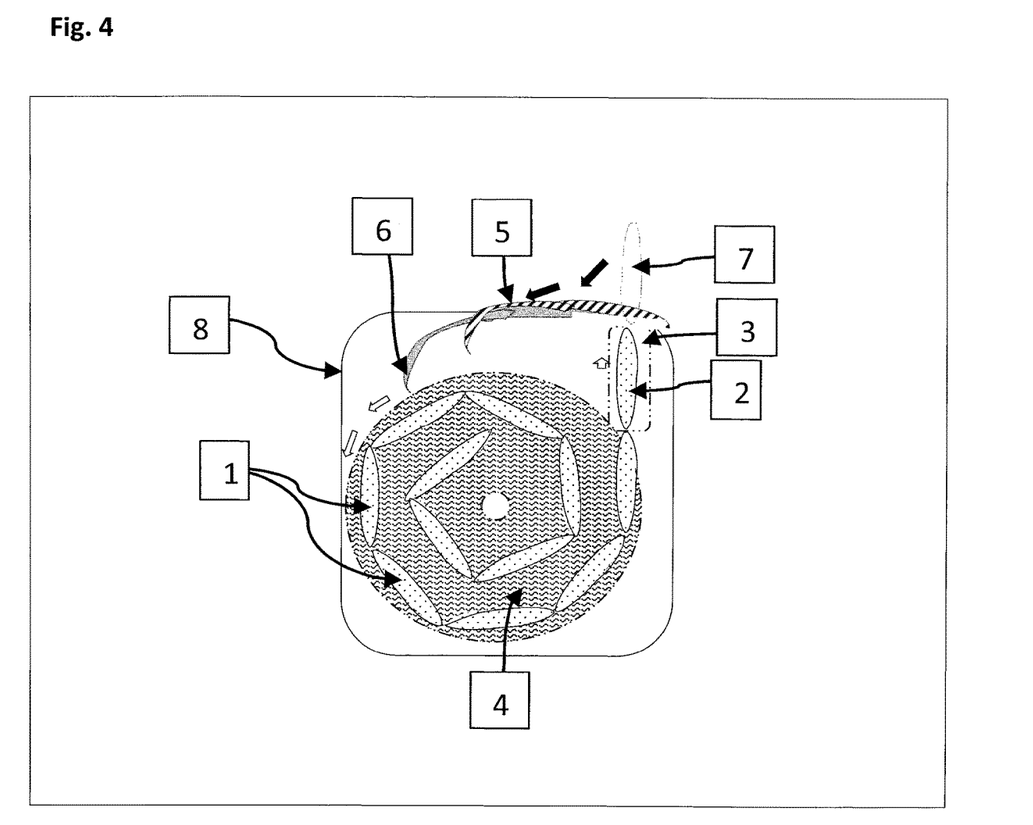

Example 19 and FIG. 4 describe a sachet dispensing container of the invention. Given the impaired dexterity of patients with neurological disorders including Parkinson's disease, a container for the sachets will be designed to include a dispensing mechanism that provides one sachet at a time. The dispensing mechanism can include a gear/disk with rough surface that provides enough friction with the sachets. Upon pushing a prominence on the side of the sachet container, an aperture will open and the same motion pushes a lever against the gear/disk. This causes the rotation of the disk and the sachets. The sachets can be arranged in a spiral of a string of sachets connected with a perforated material that is easy to break. The sachet closer to the aperture will advance though the opening for easy handling and separating by the hand or mouth. The sachet dispensing container can use mechanical mechanism or can be battery operated and equipped with a motor.

Example 20

Solubility of the medications, in certain embodiments, can be improved by reducing the particle size using customized micronization, nano-milling or spray-drying methods. (see, e.g., Chaumeil, J. C. (1998). Methods Find Exp Clin Pharmacol, 20(3), 211-215.; Kondo, M., Niwa, T., Okamoto, H., & Danjo, K. (2009). Chem Pharm Bull (Tokyo), 57(7), 657-662; Li, M., Azad, M., Dave, R., & Bilgili, E. (2016). Pharmaceutics, 8(2); and Rasenack, N., & Muller, B. W. (2002). Pharm Res, 19(12), 1894-1900.)

In certain embodiments, the sachet can contain a medication or combination of medications with particle sizes (d50–d90)=1-30 microns.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A device that comprises at least a first sachet nested inside a second sachet, wherein each sachet is made of porous, wettable and non-toxic materials, wherein the first sachet comprises an effective amount of levodopa and the second sachet comprises an effective amount of carbidopa, wherein the device is configured in a shape and size such that the device can be placed in the mouth of a human subject; wherein the second sachet is made of non-dissolvable material; and wherein the device is configured to sequentially release carbidopa and then levodopa.

2. The device of claim 1, wherein the device is configured in a shape and size such that the device can be placed in the buccal cavity of the subject.

3. The device of claim 1, wherein the second sachet is configured in a shape and size of 5-50 mm in length, 5-20 mm in width or 2-10 mm in width.

4. The device of claim 1, wherein the second sachet is made of permeable material.

5. The device of claim 1, wherein the first sachet is made of porous and permeable material.

6. The device of claim 1, wherein each sachet is made of cellulose fiber filter paper, corn fiber filter paper, carboxymethyl cellulose, or plant fiber filter paper.

7. The device of claim 1, wherein each sachet is partially filled with a non-toxic material to help maintain the bulk and shape of the device.

8. The device of claim 1, wherein each sachet is filled with a humectant material.

9. The device of claim 1, wherein each sachet is filled with excipients to improve solubility, disintegration, friability, mucosal soothing, mucosal absorption, gastrointestinal absorption and/or to adjust the acidity/alkalinity.

10. The device of claim 1, wherein each sachet is filled with dissolvable particles, spheres, pellets, granules containing medicines to control the release of medicines.

11. The device of claim 1, wherein the first sachet comprises a first combination of levodopa and carbidopa.

12. The device of claim 1, wherein the levodopa and carbidopa are micronized, nano-milled or spray-dried.

13. The device of claim 12, where in a particle size of the medication is 1-30 microns.

14. The device of claim 1, wherein the second sachet comprises an outer surface having an adhesive property.

15. The device of claim 1, wherein the second sachet is made of a material with an outer surface having an adhesive property.

16. A device that comprises at least a first sachet nested inside a second sachet, wherein each sachet is made of porous, wettable and non-toxic materials comprising cellulose; wherein each sachet comprises an effective amount of a medication selected to treat a disease or condition, the medication comprising a combination of levodopa, carbidopa and ascorbic acid; wherein the device is configured in a shape and size such that the device can be placed in the mouth of a human subject; wherein the second sachet is made of non-dissolvable material; wherein each sachet comprises mannitol.

\* \* \* \* \*